United States Patent

Holcombe, Jr.

[11] 4,068,918
[45] Jan. 17, 1978

[54] EYE COOLER FOR SUNBATHERS

[76] Inventor: Cressie E. Holcombe, Jr., 1613 Blackwood Drive, Knoxville, Tenn. 37921

[21] Appl. No.: 745,471

[22] Filed: Nov. 26, 1976

Related U.S. Application Data

[63] Continuation-in-part of Ser. No. 597,839, July 21, 1975, abandoned.

[51] Int. Cl.$^2$ .......................... G02B 3/12; G02B 1/06
[52] U.S. Cl. ........................................ 350/3; 350/2; 350/179; 351/44
[58] Field of Search ................. 351/44; 350/2, 3, 179, 350/180; 2/431

[56] References Cited

U.S. PATENT DOCUMENTS 3,161,718  12/1964  DeLuca ............................. 350/180

FOREIGN PATENT DOCUMENTS 530,375  9/1956  Canada ................................ 351/44
982,680  2/1965  United Kingdom .................. 351/44

Primary Examiner—Paul A. Sacher
Attorney, Agent, or Firm—Martin J. Skinner

[57] ABSTRACT

An eye cooler is described to minimize discomfort of the eye region during sunbathing and, at the same time, to permit tanning of the area covered by the cooler. This is accomplished using a pair of flexible liquid-filled lenses, the walls of the lenses being formed from a very thin plastic film. The lenses are joined to each other by a nose bridge section, and means are included to hold the cooler in place on the wearer in contact with the skin. The liquid within the lenses, such as water, serves as a heat sink whereby heat is transferred through the thin plastic from the skin into the water to provide the cooling effect.

In a special embodiment, the plastic and the liquid are chosen so as to provide a desired degree of transmission of the ultraviolet radiation wavelengths which produce tanning. The u.v. transmission of the total lens can be made equivalent to that of suntanning preparations, for example.

6 Claims, 5 Drawing Figures

EYE COOLER FOR SUNBATHERS

This is a continuation-in-part application of my earlier filed application Ser. No. 597,839, filed July 21, 1975 now abandoned.

BACKGROUND OF THE INVENTION

My invention relates generally to eye covers and more particularly to an eye cooler for use during sunbathing whereby the eye region of the face is maintained at a comfortable temperature and receives sufficient ultraviolet radiation to permit tanning to match the remainder of the wearer's face.

Because of the sensitivity of the eyes and eye region, sunbathers have long been faced with the problem of the discomfort to the eyes when the face is directed toward the sun, particularly when the eyes are unprotected so as to permit tanning the eyelids. This heating problem arises from solar heating of the skin. With a comfortable skin temperature of about 32° C, the solar radiation absorption could increase the outer skin temperature by about 5° C. Although normal body thermoregulation measures (blood circulation, perspiration, etc.) attempt to cool the skin, overheating can occur, and the nervous system rapidly detects this as discomfort. The sunbather usually minimizes the heating by shading the eyes, or by turning a different portion of the body toward the sun. In general, a sunbather may reposition the body every 10–15 minutes in bright sun: less often on a cloudy day. When eye protection is worn, as with a cloth or darkened glasses, the eyelids and any area shaded by the protection remain pale. For persons who wish to attain a substantial tan, this "white eye" effect is not appealing.

Moistened pads are the common means to provide any relief from the heat discomfort as tinted glasses give little relief. Typical of the prior art are the compresses or pads described in U.S. Pat. No. 3,527,947. Any of these must be periodically remoistened and, as discussed above, leave the sunbather with untanned areas around the eyes.

Accordingly, it is desirous to provide an eye cooler that will keep the eyes comfortable for reasonable periods of time during sunbathing and still accomplish a desired degree of tanning about the eyes.

SUMMARY OF THE INVENTION

Figure 1:
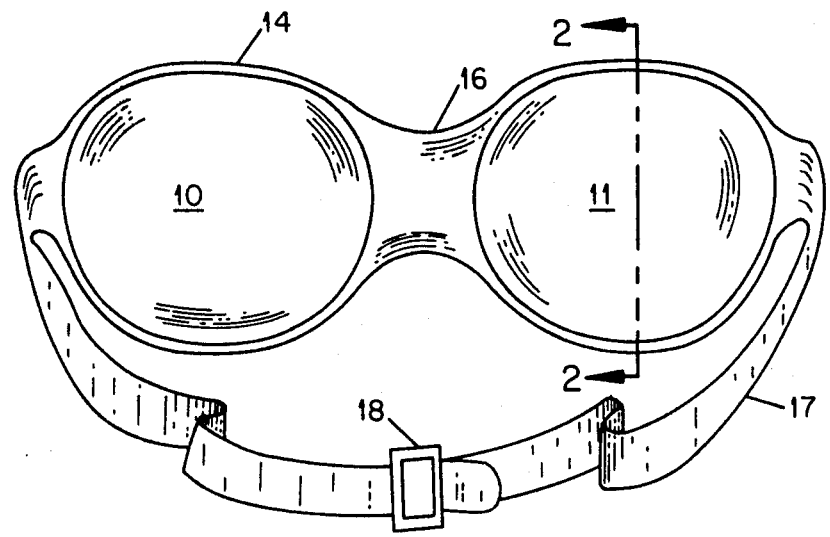
FIG. 1 is a frontal view of one embodiment of my eye cooler.

My eye cooler accomplishes the purpose of maintaining eye comfort for reasonable time periods through the use of liquid-filled lenses which contact the eyelids and other skin of the eye region when worn. The unframed lenses are fabricated from thin flexible plastic whereby each lens is in contact with a substantial portion of skin beneath the lens. There is sufficient liquid in each lens to provide a heat sink whereby the heat exchange produces a cooling effect upon the skin for a reasonable length of sun exposure before the liquid must be re-cooled. Each lens may be subdivided to enhance conformity to the surface of the face, and the lenses are joined so as to bridge the nose. Flexible ties or an elastic strap may be attached at the outer edge of each lens whereby the eye cooler may be held in place on the wearer's head with the lenses in substantial contact with the skin. The plastic and/or the liquid may be selected to give a desired degree of ultraviolet radiation transmission to achieve optimum tanning.

DETAILED DESCRIPTION

The objective of my invention is to provide an inexpensive, flexible eye cooler for sunbathers in which sealed plastic pouches or lenses contain a liquid to create a cooling effect upon the eyes and skin about the eyes. This cooling is the result of heat transfer, by conduction, from the skin through the plastic into the liquid. The liquid is present in sufficient quantity to act as a "sink" for this heat, as well as that intercepted from the incoming sun's rays. Movement of the liquid, through circulation, improves heat transfer from the plastic interior surface into the liquid. The entire lens transmits a sufficient amount of the ultraviolet (u.v.) radiation wavelengths which cause tanning of the skin in order to permit reasonable rates of tanning beneath the eye cooler.

My invention is best described with reference first to FIGS. 1 and 2. The eye cooler has a pair of lens elements 10, 11, each of which is formed by two layers of thin flexible plastic 12, 13 sealed to each other around the periphery as at 14 using conventional plastic joining techniques. This results in an unframed set of lenses. The volume 15 between the layers is filled with water or other suitable heat exchanging fluid. The lenses 10, 11 are joined to each other with a nose bridge section 16 which may be of the same plastic. If desired, the nose bridge section 16 may be filled with a liquid; however, the nose region is less sensitive to heat. Attached to the outer edges of the lenses is a strap 17 or other suitable headcircling (head band) element so as to retain the lenses of the eye cooler in proper place against the skin whether the wearer is reclining or is in an upright position. A buckle 18 or other adjusting means may be included in the strap 17. This strap also may be fabricated from the same plastic as the lenses. Alternatively, an elastic band may be used without the necessity for a separate adjusting means. It should be noted that I use no rigid frames, rigid ear pieces or the like, all of which would hinder contact of the lenses with the skin.

Figure 2:
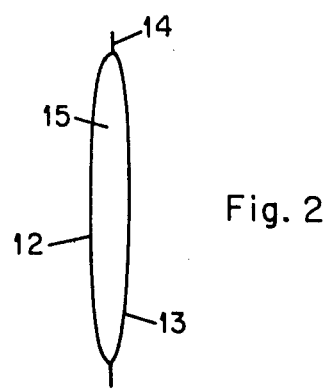
FIG. 2 is a cross section of one lens of the embodiment of FIG. 1 taken at 2—2 thereof.

A substantially flat lens, as shown in FIG. 1, may not conform adequately to the face of a wearer: there may be relatively large areas where little cooling will occur due to the lack of contact. Also, the liquid will tend to move to outer edges of the lenses when the user is reclining due to gravitational forces and due to the flexibility of the plastic. This leaves regions of less liquid for cooling at the inner edges of each lens.

Figure 3:
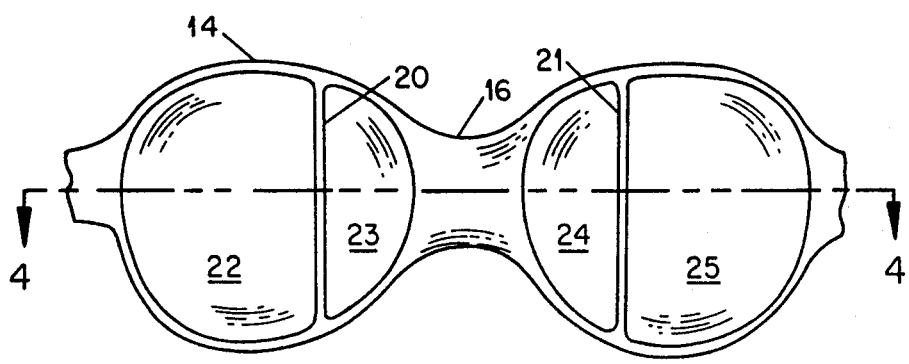
FIG. 3 is a frontal view of another embodiment of my eye cooler.
Figure 4:
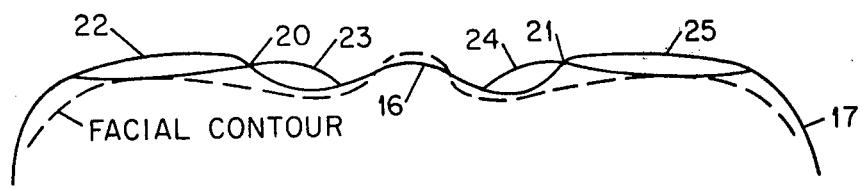
FIG. 4 is a cross sectional view of the embodiment of FIG. 3 taken at 4—4 thereof.

The embodiment shown in FIG. 3 reduces these adverse effects. In this embodiment each lens is subdivided into compartments 22, 23 and 24, 25 by partitions or barriers 20, 21 created by joining the plastic layers 12, 13 to each other along a narrow line. These barriers 20, 21 are sufficiently narrow so as to not affect the cooling capacity of the lens, and the lens can bend at this line thereby increasing contact with the skin. Each barrier is oriented substantially perpendicular to the bridge 16 and located at a position whereby the portion of the lens nearer the bridge (e.g., portion 23) is about one-third to one-half the volume of the outer portion (e.g., portion 22). As a result, each lens will more accurately conform to a facial profile, as shown in FIG. 4, and the liquid will be retained better in all portions of the lenses.

Although several fabrication methods may be utilized to fabricate my eye cooler, one of the least expensive involves overlaying two sheets of plactic which will form the lenses and nose bridge. The lens may be of any desired shape, e.g., circular, oval, hexagonal, etc. The plastic sheets are then heat-sealed around the perimeter of the lenses, and across the bridge, leaving a small passageway to communicate with the interior of each lens. The layers may also be joined using a conventional cement.

In an alternative construction, the bridge member may be formed from a separate section of plastic and joined to fabricated lens units. Thereafter, water or another liquid is inserted into the interior of each lens, completely filling the same at substantially atmospheric pressure. A hypodermic needle, for example, may be used for this filling operation. The passageways are then sealed using a heat sealing technique, cement, etc.

The plastic for the lenses and other structural portions of the preferred embodiments of my eye cooler is chosen using three principle criteria: flexibility, thickness and u.v. transmission. The first two criteria are inter-related. A highly flexible film is necessary adjacent the skin in order to maximize the fractional contact area that allows conduction while keeping air gaps uniform and small. If the noncontact areas are not small and uniform in spacing, regions of the skin can rise in temperature because the skin has poor thermal conductivity. Furthermore, a highly flexible plastic is more comfortable against the skin. Of course, reduced thickness is an aid to providing this flexibility.

In order for my eye cooler to be effective, heat must be transferred from the skin, through the plastic layer in contact with the skin, into the liquid. Furthermore, the liquid must remain at a temperature below that of the skin for time periods approximately matching the time periods a sunbather faces the sun before turning in another direction, e.g., 10–15 minutes in a hot sunshine. The thermal resistance to heat flow of the skin-contacting plastic is expressed by the approximate equation: $R = \Delta x k A f$; where $\Delta x$ is the plastic thickness, $k$ is the thermal conductivity of the plastic, $A$ is the area of the plastic and $f$ is the fractional area of contact with the skin. Thus, it may be seen that the resistance, $R$, is directly proportional to the plastic thickness since the heat is transferred through the plastic by conduction. Similar equations express the thermal resistance to heat transfer through other regions affecting eye cooling where conduction is the mode of heat transfer: skin region (contacting the plastic) and plastic region contacting the ambient air. Heat transfer in the liquid region and by the ambient air contacting the plastic is by convection, with thermal resistances to heat flow of the form: $R = 1/hA$, where $h$ is the convection heat transfer coefficient.

For any region of the eye cooler, the rate of heat transfer, $q$, may be expressed as $q = \Delta T/R$, where $\Delta T$ is the temperature differential over the region of heat flow. Assuming a typical temperature differential (e.g., 16° C) between the skin and the liquid of the eye cooler, a plastic area of about 20 cm² (3.1 in²), and a fractional contact area of 30%, heat transfer rates may be calculated. With an average liquid thickness of 0.635 cm (0.25 in), the liquid volume is about 12.7 cm³ (0.775 in³). Such a water volume will act as a heat sink and thus provide cooling capability for 6 to 12 minutes (depending on the solar radiation level) before exceeding the comfortable skin temperature. At this point, the eye cooler must be recooled to again become effective. In order to avoid the overheating of the skin for a high solar radiation level, it is necessary that the plastic film adjacent the skin conduct heat from the skin into the water at a faster rate than heat would be absorbed by the skin. For the eye cooler described above, a calculated maximum plastic thickness of 0.25 mm (0.01 in) could provide the necessary transfer of heat away from the skin. Plastics of any greater thickness will, therefore, permit essentially no cooling under conditions of maximum solar heat input. The lower limit of plastic film thickness is set, primarily, by resistance to damage during handling. This lower limit is about 0.02 mm.

In actual sunbathing, eye coolers with 0.02 to 0.25 mm thick plastic films were tested under approximately the same conditions. The plastic films below 0.05 mm were generally too limp. Plastic films of >0.15 mm thickness provided less contact with the skin and thus provided less uniform cooling than the thinner films. As previously mentioned, both the area of contact and the uniformity of contact are necessary to prevent air gaps and regions of overheating of the skin. The required heat transfer capability and uniformity of the heat transfer appear to be best achieved with flexible plastic films in the thickness range 0.05 to 0.15 mm; however, an operable range is 0.02 to 0.25 mm.

Calculations show that the convection heat transfer from the ambient air (and thus the ambient air temperature) is relatively unimportant to the cooling process of the eye cooler. Therefore, eye coolers of appropriate plastic thickness, flexibility and liquid volume will effectively cool the skin in the region of the eyes. Furthermore, it should be pointed out that the thickness of the plastic toward the air is not as critical for heat transfer. However, to provide for the overall flexibility of the cooler and to eliminate designating the side to be worn against the skin, it is preferred that both plastic layers have the same thickness.

The quantity of liquid, and particularly the thickness thereof, is a significant parameter in the effectiveness of my eye cooler. The liquid receives heat input from two sources: the skin (if the plastic is sufficiently thin) and the solar radiation. If solar radiation raises the temperature of the liquid to that of the skin, no further cooling of the skin can occur. Since the heat rise of the liquid due to solar radiation is proportional only to liquid thickness (for a given set of conditions), the time required to raise the liquid temperature to that of the skin (overheat condition) can be calculated for different lens thicknesses. Using data for the maximum level of solar radiation input (high noon, optimum conditions), it may be shown that a 4 mm thickness of water will overheat in about 4 minutes; a 6.35 mm (0.25 in) lens would overheat in about 6 min. At a thickness of 10.7 mm, the time increases to 10 minutes. Longer time durations will exist before overheating conditions occur for lower solar input. Typically, the range is 50–80% of the maximum input. Thicknesses greater than about 10 mm may exert an uncomfortable pressure on the eyes when the sunbather is reclining. With these considerations, a range of about 4 to 10 mm is suitable for the lens thickness of my eye cooler.

The area of the cooler is important only with regard to the area of skin to be cooled. About 10 cm² (1.55 in²) is about minimal to cover the eyelid region, assuming a circular lens. A practical upper limit is about 30 cm² (4.65 in²) although this is not extremely critical. It should be noted that lenses of larger areas increase the problem of obtaining a high degree of contact with the skin of the eye region.

As stated above, it is desired that the lenses of my eye cooler transmit a reasonable degree of the ultraviolet radiation which brings about sunburn (erythema) and/or tanning (pigmentation). This u.v. radiation is in the range of about 2970A to 3300A for combined erythema and pigmentation; or for a greater degree of pigmentation, from 3150A to 3300A. These ranges of radiation are well known in the art and are considered in preparing suntanning lotions and the like. If suntanning (sunscreening) preparations are normally used by the wearer of my eye cooler, the lenses thereof need only transmit about 10% of the u.v. radiation to match that of the suntanning preparation. If no suntanning preparations are used, the lenses should transmit at least about 50% of the important u.v. radiation wavelengths. Either of these conditions will permit tanning of the eyelid area to about the same extent as the remainder of the face.

In addition to the foregoing characteristics of the plastic, there are certain other prerequisites. For example, a suitable plastic has a very low permeability for water or any other liquid to be used in the lenses, and must be unreactive with these liquids. Furthermore, the plastic film should be clear and the surface shiny in appearance to enhance desired ultraviolet radiation transmission. Primarily for appearance, it should be noted that the plastic used for the eye cooler may be slightly tinted, e.g., green, gray, etc. Alternatively, a tint may be added to the liquid within the lenses.

Several thermoplastics are known in the art which exhibit the desired characteristics. These are described, for example, in "1974–1975 Modern Plastics Encyclopedia", Vol. 51, No. 10A (Oct. 1974). Polyethylene and fluoroplastics, such as fluorinated ethylenepropylene (FEP) transmit about 90% of the u.v. radiation of the wavelengths of interest, i.e., 2970A to 3300A. A typical FEP is DuPont Teflon. Another class of suitable plastics are ionomers which are defined in the cited encyclopedia as a class of polymers in which ionized carboxyl groups create ionic crosslinks in the intermolecular structure. One such ionomer is "Sur-Flex" produced by Flex-O-Glass, Inc., 4647 W. Augusta, Chicago, Illinois. This is believed to be formed using a DuPont ionomer resin "Surlyn". Ionomer resins are also produced by Union Carbide Corp., Ametek/Westchester Plastics and LNP Corporation. Ionomers have an ultraviolet transmission of about 75–85% in the range of interest, are extremely flexible but durable, and are highly resistant to attack by common chemicals. For testing purposes, I have primarily used the ionomer "Sur-Flex", particularly because of the flexibility of ionomers: any other ionomer would be suitable.

The presence of a water layer decreases the ultraviolet transmission when using any of the above-identified plastic films. For example, the transmission of 3150A through the test ionomer lenses was about 45% for films having the thicknesses in the preferred range, i.e., thicknesses of 0.05–0.15 mm. The amount of water had little effect upon the transmission in the range of 4 to 10 mm. The transmission through equivalent thicknesses of film and water using FEP and polyethylene was approximately the same as for the ionomer; namely, about 50%.

An ideal plastic, or plastic-liquid combination, would be one that has a cutoff transmission point at about 3150A; i.e., has a reasonable transmission above that wavelength but a low transmission at lower wavelengths. This would provide for pigmentation with minimal erythema. No plastic alone is known which has this characteristic; however, liquids can be modified to provide this feature for my eye cooler by adding sunscreening agents which reduce transmission of low u.v. wavelengths. These agents are typically chosen from the group p-aminobenzoic acid, salicyclic acid, cinnamic acid and benzophenone, or their derivatives. This art is described, for example, in U.S. Pat. No. 3,341,419 to H. J. Eiermann, et. al., issued Sept. 12, 1967. Two recently publicized screening agents for application to the skin are 4.5% p-dimethyl aminobenzoic acid and 2.7% alkyl p-aminobenzoate. For example, a dilute solution of para-aminobenzoic acid (PABA) dissolved in water or alcohol may be used.

Various dilute concentrations of PABA in water were tested using 0.05 mm thick ionomer plastic with the liquid thickness being 5 mm. The u.v. transmission of such lenses was determined and the results are shown in the following table at four wavelengths. It may be seen from the data in the table that a water solution containing p-aminobenzoic acid in low concentrations of 0.05 to 0.15 g/l (0.005 to 0.015 wt %), can act as a cutoff point liquid for shorter wavelength u.v. radiation, i.e., below 3150A, and permit passage of longer wavelengths u.v. in natural sunlight. PABA is a vitamin which is nontoxic and unreactive to plastics. The transmission at wavelengths above 3300A has little effect upon the skin. When the eye cooler is used during exposure to artificial solar radiation (sun lamps), a more concentrated solution (even up to saturation) may be desirable due to the higher proportion of lower wavelengths in lamp radiation.

| Concentration of PABA (g/l) | Percent Transmission at Wavelengths | | | |
|---|---|---|---|---|
| | 3600A | 3300A | 3150A | 2970A |
| Zero | 67 | 65 | 63 | 59 |
| 0.05 | 62 | 56 | 22 | 0.6 |
| 0.10 | 57 | 50 | 10 | 0.2 |
| 0.15 | 48 | 35 | 3 | 0.2 |
| 5.9 (Saturated) | 44 | 0 | 0 | 0 |

My invention is of principal value when worn during sunbathing; however, there are other instances where cooling of the eyes is beneficial. Such instances include the treatment of tired eyes, headaches, discomfort of the eyes caused by a fever, etc. For these other applications the degree of u.v. transmission is not a factor; however, the criteria regarding uniformity of heat transfer are applicable. The plastic may be opaque for these applications.

Figure 5:
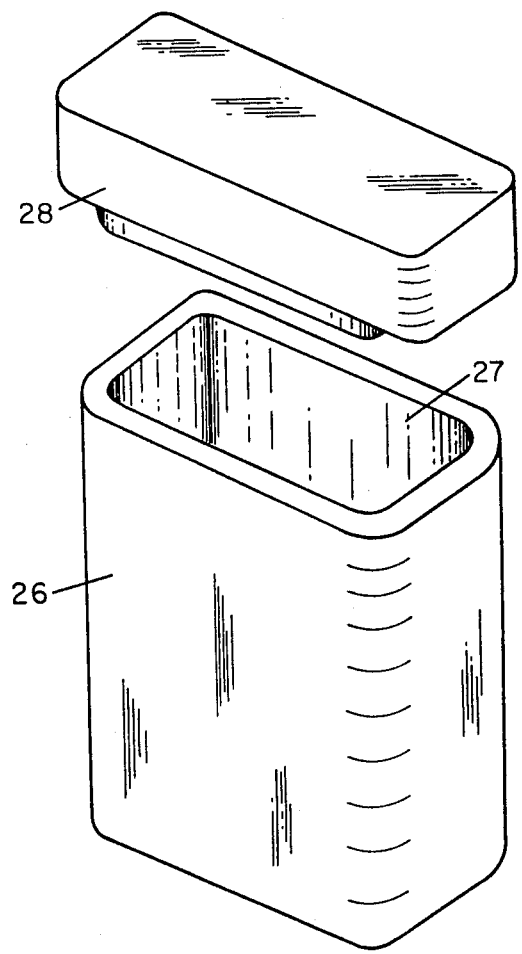
FIG. 5 is an isometric view of a carrying case for my eye cooler.

It will be apparent that the most effective value of my eye cooler will be achieved if the cooler is at a temperature lower than the skin prior to use. Accordingly, it is desirable to provide an enclosure for the cooler when not in use. Such an enclosure is illustrated in FIG. 5. This comprises a body 26 having a cavity 27 of sufficient volume to receive one or more folded eye coolers, and a cover 28 which may be hinged to the body 26 or completely removable, as shown. Both the body and cover would be fabricated from an insulating type material, such as Styrofoam. This enclosure would then be suitably carried in an iced cooler, beach bag, purse, etc. The carrier would also provide physical protection to prevent puncture of the lenses.

As an alternate method of reducing the temperature of the eye cooler below that of the skin and the ambient air, my eye cooler may be immersed periodically in cool water (e.g., 20° C) to renew its effectiveness for cooling the eyes. Typically, an eye cooler at 32° C returns to 20° C in about 30 seconds when so immersed. For the sunbather, this can be done whenever the body is reoriented so that the eyes are turned from the direction of the sun. The cooler is thus ready for use when the sunbather again faces the sun.

I claim:

1. An eye cooler for providing comfort to skin of the eye region, and thus the eyes of a wearer, the cooler having a size and flexibility sufficient to conform to and contact a substantial portion of the eye region skin, which comprises: a pair of unframed lenses, each lens being formed from two overlying sheets of a flexible plastic film sealed to each other about their periphery thereby forming an internal volume, at least one of the sheets of plastic film having a thickness of about 0.02 to 0.25 mm; a liquid at substantially atmospheric pressure completely filling the interior volume of each lens, the liquid being of sufficient quantity to produce a lens thickness of about 4 to 10 mm; a nose bridge of flexible plastic film connected between adjacent edges of the lenses; and a flexible head band attached to opposite edges of the lenses for retaining the lenses of the eye cooler in contact with the eye region skin of the wearer.

2. The eye cooler of claim 1 wherein the plastic of the lenses and nose bridge has a thickness of 0.05 to 0.15 mm and wherein the liquid is water.

3. The eye cooler of claim 1 wherein each lens is divided into first and second liquid-filled portions by a partition oriented substantially perpendicular to the nose bridge at a position where the first liquid-filled portion nearer the nose bridge is about one-third to one-half the volume of the second liquid-filled portion.

4. The eye cooler of claim 1 wherein the lenses and nose bridge transmits at least 10% of ultraviolet radiation in a range of 2970A to 3300A.

5. The eye cooler of claim 4 wherein the plastic is selected from the group of thermoplastic resins consisting of polyethylene, fluorinated ethylene-propylene and ionomers.

6. The eye cooler of claim 1 wherein the plastic is an ionomer and wherein the liquid is a 0.005 to 0.015 wt % solution of para-aminobenzoic acid in water.

* * * * *